United States Patent [19]
Bayer et al.

[11] Patent Number: 5,420,290
[45] Date of Patent: May 30, 1995

[54] NITROSAMINE-FREE 3-ISOTHIAZOLONES AND PROCESS

[75] Inventors: Horst O. Bayer; Barry C. Lange, both of Levittown; Ramesh B. Petigara, Hatfield, all of Pa.

[73] Assignee: Rohm and Haas Company, Philadelphia, Pa.

[21] Appl. No.: 154,664

[22] Filed: Nov. 18, 1993

Related U.S. Application Data

[60] Division of Ser. No. 970,971, Nov. 2, 1992, Pat. No. 5,312,827, which is a continuation of Ser. No. 728,438, Aug. 12, 1991, abandoned, which is a division of Ser. No. 500,158, Mar. 27, 1990, Pat. No. 5,068,338, which is a division of Ser. No. 376,199, Jul. 3, 1989, Pat. No. 4,939,266, which is a continuation of Ser. No. 383,858, Jul. 20, 1989, Pat. No. 5,090,428.

[51] Int. Cl.$^6$ ............................................. C07D 275/03
[52] U.S. Cl. ..................................................... 548/213
[58] Field of Search ......................................... 548/213

[56] References Cited

U.S. PATENT DOCUMENTS

| | | | |
|---|---|---|---|
| 3,285,930 | 11/1966 | Williams | 260/302 |
| 3,341,547 | 9/1967 | Malley | 260/302 |
| 3,523,121 | 8/1970 | Lewis | 260/306.7 |
| 3,829,580 | 8/1974 | Bayer | 568/138 |
| 3,957,808 | 5/1976 | Miller et al. | 260/302 A |
| 4,150,026 | 4/1979 | Miller | 260/299 |
| 4,508,908 | 4/1985 | Virgilio et al. | 548/213 |
| 5,008,395 | 4/1991 | Petigara | 548/213 |
| 5,068,338 | 11/1991 | Bayer et al. | 548/101 |

FOREIGN PATENT DOCUMENTS 490564  6/1992  European Pat. Off. ............ 548/213

OTHER PUBLICATIONS

Wallace et al., Base-Catalyzed Elimination Studies on Sulfones, Sulfoxides, Sulfides, Disulfides, and Mercaptans in Dimethyl Sulfoxide, J. Am. Chem. Soc., vol. 85, (1964), pp. 2739-2743.

H. T. Clarke and J. M. Inouye, The Journal of Biological Chem., vol. 89, pp. 399 to 419, (1930).

Haefele et al., The Synthesis and Properties of Mercaptans Having Different Degrees of Audity of the Suphydnyl Goup, Proceedings of Scientific Section, No. 32, 52-59 (1959).

Tarbell et al., Cleavage of the Carbon-Sulfur Bond in Divalent Sulfur Compounds, Chem. Reviews, vol. 49, pp. 6-7; 11-12 (1951).

Anselme, The Organic Chemistry of N-Nitrosamines: A Brief Review, N-Nitrosames, ACS Symposium Series 101, American Chemical Society, Washington D.C., pp. 1-3 (1979).

Reid (Editor) Organic Chemistry of Bivalent Sulfur, Chemical Publishing Co., Inc., New York, pp. 110-111 128-129, 462-463 (1958).

Bruchhausen, Die Neuheit von Stofferfindungen Gegenuber Allgemeinen Formeln und dergleich in Gewerblicher Rechtsschutz und Urheberrecht, pp. 226-230 (1972).

Friedman et al., Addition Reactions with alpha, beta-Unsaturated Compounds, J. Am. Chem. Soc, vol. 87, pp. 3672-3682, (1965).

U.S. Federal Register, vol. 45, No. 124 (25 Jun. 1980).

Swan, Nature, 11 May 1957, p. 965.

Danehy et al., The Alkaline Decomposition of Organic Disulfides I. Some Dithiocarboxylic Acids J. Amer. Chem. Soc., vol. 83 (1961), pp. 1109-1113.

Chemistry & Industry, 16 Oct. 1965, p. 1769, Wallace et al.

Organikum, 13 K Edition (1964), VEB Deutscher Verlag der Wissenschaften, Berlin, p. 470.

W. D. Crow, et al., J. Org. Chem., vol. 30 (1965), pp. 2660-2665.

(List continued on next page.)

Primary Examiner—Robert Gerstl
Attorney, Agent, or Firm—Michael B. Fein

[57] ABSTRACT

Nitrosamine-free 3-isothiazolone biocidal compositions suitable for applications where substantial human or animal contact is anticipated, their method of use and process of preparation are disclosed.

7 Claims, No Drawings

OTHER PUBLICATIONS

Nicolet, The Meshaniam of Sulfur Lability in Cysteine and Its Derivatives, I. Some Thio Ethers Readily Split by Alkali; J. Am. Chem. Soc., vol. 53, pp. 3066–3072 (1931).

Krzeminski, et al., Fate of Microbicidal 3–Isothiazolone Compounds in the Environment: Modes and Rates of Dissipation, Agricultural And Food Chem., vol. 23, pp. 1060–1068 (1975).

Krzeminski, et al., Fate of Microbicidal 3–Isothiazolone Compounds in the Environment: Products of Degradation, Agricultural and Food Chem., vol. 23, pp. 1068–1075 (1975).

Rompps Cheme–Lexicon, 7 Edition (1974), p. 2575.

NITROSAMINE-FREE 3-ISOTHIAZOLONES AND PROCESS

This is a divisional of application Ser. No. 970,971, filed Nov. 2, 1992, now U.S. Pat. No. 5,312,827, which in turn is a continuation of Ser. No. 728,438 filed Aug. 12, 1991, now abandoned, which in turn is a division of Ser. No. 500,158 filed Mar. 27, 1990, now U.S. Pat. No. 5,068,338, which is a division of Ser. No. 376,199 filed Jul. 3, 1989, now U.S. Pat. No. 4,939,266, which in turn is a continuation of Ser. No. 383,858 filed Jul. 20, 1989 now U.S. Pat. No. 5,090,428.

This invention is directed to 3-isothiazolone compositions containing little or no nitrosamine impurities making them-especially suitable for cosmetic and drug applications, their method of use and the processes by which the products are made nitrosamine-free.

The 3-isothiazolones comprise a large group of biologically active pesticides exhibiting biostatic and/or biocidal activity towards many pests of both animal and vegetable origin, such as fungi, bacteria, algae, slime, barnacles, mildew and the like (see U.S. Pat. No. 3,761,488). These compounds may be represented by the following general formula:

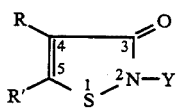

wherein R and R' are independently selected from hydrogen, halogen or an alkyl group of 1 to 4 carbon atoms; Y is an alkyl group of 1 to 8 carbon atoms, a cycloalkyl group of 3 to 6 carbon atoms, an aralkyl group of up to 8 carbon atoms, or an aryl or substituted aryl group of 6 carbon atoms.

When the 3-isothiazolone is one in which Y (see formula above) is lower alkyl, and at least one of R and R' is halogen (with the other, usually R, a hydrogen), the compounds are useful industrial biocides having almost unlimited solubility in water (see U.S. Pat. No. 4,105.,431). The less water-soluble, higher alkyl 3-isothiazolones are generally useful as mildewcides and fungicides in organic solutions and emulsion products such as paints; the higher alkyl isothiazolones are soluble in various organic solvents such as ethanol, isopropanol, acetone and the like. Such solutions may be easily extended with water. Isothiazolones are also used in solid form, preferably absorbed on or in a particulate carrier.

Unfortunately, solutions of the 3-isothiazolones, especially aqueous solutions or solutions in polar organic solvents such as alcohols, are unstable, leading to reduced biological effectiveness.

This is especially true of the lower alkyl analogs, that is, where Y above is a $C_1$-$C_4$ alkyl or a cycloaliphatic radical. The instability results from an opening of the isothiazolone ring to form linear compounds which do not have the same biological properties as the ring compounds. To inhibit ring cleavage, nitrate salts, particularly those of polyvalent metals such as calcium, copper, magnesium, manganese, nickel and zinc, can be added to isothiazolone solutions. Thus it is commercially desirable today to formulate many of the 3-isothiazolone biocides in solutions containing water or organic solvent or mixtures thereof together with nitrate stabilizers to prevent decomposition of the 3-isothiazolone (see U.S. Pat. No. 3,870,795).

The effectiveness of the 3-sothiazolone biocides at very low use levels has encouraged further commercial use in products intended for human contact such as topically applied cosmetics, thus creating greater requirements for purity than previously needed for industrial applications.

The existing commercial process used for manufacturing 3-isothiazolones has included amidation of a disulfide followed by the halogenation cyclization of the disulfide amide:

Amidation

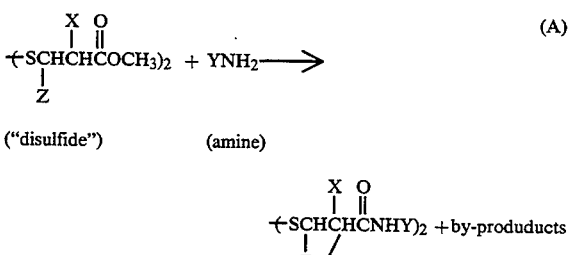

Cyclization

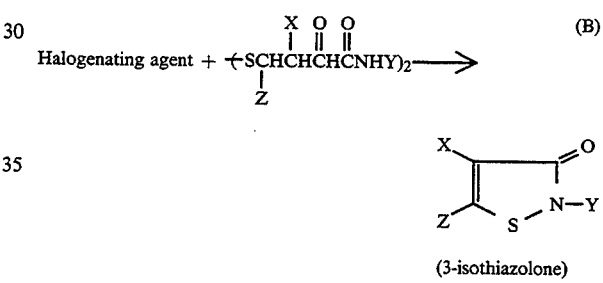

wherein X and Z (R and R' in the general formula, except for halogen later attached) are hydrogen or lower alkyl and Y is as set forth in the above general formula.

Cyclization is accomplished by contacting the amide with a halogenating agent. Typical halogenating agents include chlorine, bromine, sulfuryl chloride, sulfuryl bromide, N-chlorosuccinimide, N-bromosuccinimide, and the like. Chlorine and sulfuryl chloride are the preferred halogenating agents. For most industrial purposes the amidation of the disulfide intermediate (hereinafter "disulfide") produces the amide intermediates (hereinafter "amide") and ultimately the 3-isothiazolone compounds of relatively high purity. When prepared according to the above reactions (A) and (B), the 3-isothiazolones are generally mixtures comprising two or more active ingredient (AI) isothiazolone species together with various by-products, including some amines which have not heretofore been characterized. The term "isothiazolone" is alternatively used herein and in the claims to refer to individual species or, collectively, to refer to reaction mixtures comprising a plurality of biologically active compounds.

We have now discovered that certain 3-isothiazolone biocides produced using the prior art disulfide intermediate may contain by-product impurities having a secondary or tertiary amine group which, upon exposure to nitrosating conditions, can be converted to nitroso compounds. As a group, nitroso compounds are generally suspected to be possible carcinogens. Accordingly, it is desirable to find means for eliminating even the trace quantities of those by-product impurities which serve as precursors to the formation of nitrosamines, especially for products to be used in applications where human or animal contact is anticipated.

The nitrosamine problem is exacerbated when formulating 3-isothiazolone compositions in solutions, either aqueous solutions or organic solutions or mixtures thereof wherein it is necessary to incorporate a nitrate salt, see, e.g., U.S. Pat. No. 4,067,878, or where another nitrosating agent may be present in the isothiazolone. When the metal nitrate salt is present as a stabilizer, any by-product secondary or tertiary amine compound present in the 3-isothiazolone reaction mixture is subject to being nitrosated to a nitroso compound which may be suspected to be carcinogenic. The expression "nitrosamine precursor", or simply "precursor", is intended to identify a secondary amine (and if present, a tertiary amine) by-product compound which can be converted to a nitrosamine.

It is an object of this invention to prepare certain 3-isothiazolone compositions free of nitrosamine precursors or nitrosamines.

It is another object of this invention to prepare aqueous 3-isothiazolone solutions which are substantially free of nitrosamines or nitrosamine precursors that can be converted to nitrosamine compounds.

It is a further object of the present invention to furnish processes for making 3-isothiazolones which either inhibit the formation of nitrosamine precursors or, alternatively, which can be utilized to remove nitrosamine precursors before they are subjected to nitrosating conditions.

Further objects will be obvious from the description which follows.

Except where stated otherwise herein, all percentages are by weight.

In preparing industrial biocides by amidation of the usual disulfide intermediates (e.g., dimethyl-3,3-dithiodipropionate), we find typical levels of nitrosamine precursors between about 0.5% (5,000 ppm) and about 1.1% (11,000 ppm) by weight in the amide product (the amide). After the amidated intermediate is chlorinated, filtered, neutralized, dissolved in water together with a metal nitrate Stabilizer and heat-treated to remove by-product impurities, the final product contains about 6%–16% (by weight of the original precursor) of a nitrosamine, that is, in the case of an original precursor content of 5,000 ppm, the final product has been found to contain typically 750 ppm of nitrosamine. Because of the high dilution factor in industrial applications, under use conditions the nitrosamine is rarely present in concentrations greater than parts per billion.

Among the most effective biocides for inhibiting bacterial growth is a 3-isothiazolone mixture comprised mainly of 5-chloro-2-methyl-4-isothiazolin-3-one and 2-methyl-4-isothiazolin-3-one (mixture dependent upon chlorination conditions), wherein the chlorinated species is between 60% and 90% by weight of the total active ingredients (AI). The process of manufacture includes the following:

Amidation

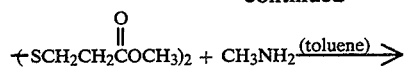

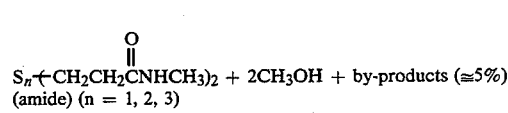

Chlorination (Cyclization)

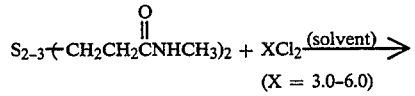

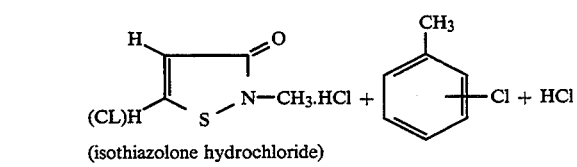
(isothiazolone hydrochloride)

Neutralization

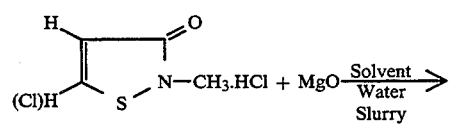

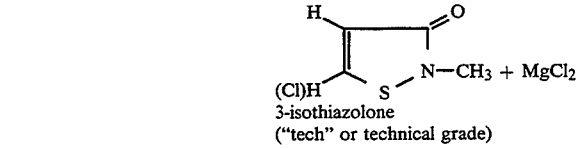
3-isothiazolone
("tech" or technical grade)

The first reaction above (1) produces a mixture containing about 95% mono-, di- and tri-thiodiamides and methanol. Upon cleavage of the disulfide (during amidation), N-methylacrylamide by-product is believed to be formed. Conjugate addition of monomethylamine to this cleavage by-product may lead to the formation of the principal nitrosamine precursor, N-methyl-3-(N'-methylamino) propionamide, by the following probable reaction:

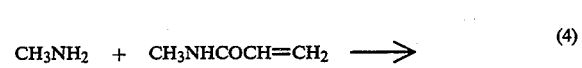

CH$_3$NHCH$_2$CH$_2$CONHCH$_3$
(nitrosamine precursor, MMAP)

N-methylacrylamide will also theoretically add to MMAP produced by reaction (4) above according to the following:

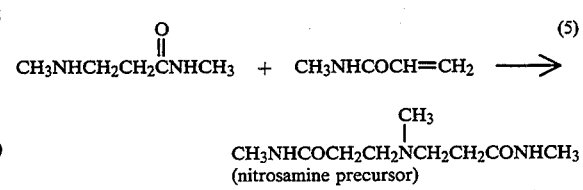

Both of the above nitrosamine precursors have been identified as being present in the intermediate amide produced when amidating a disulfide starting material. The nitrosamine precursors remain with the AI through chlorination, neutralization and formulation of the 3-isothiazolone composition until the metal nitrate salt is added, at which time nitrosation takes place (principally during heat treatment) to form a nitrosamine, e.g.:

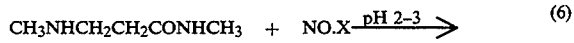

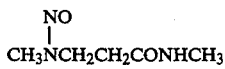

The amidation reaction (1) is conducted in an organic solvent, either aliphatic or aromatic or mixtures thereof. Illustrative of the solvents used are methanol, toluene and laktane. Laktane is a commercial (Exxon) hydrocarbon solvent with a flash point of 25° F., a b.p. range of 102°–108° C., and having the composition:

| paraffins | 28% w/w |
| cycloparaffins | 54% w/w |
| toluene | 18% w/w |

The disulfide amide reaction mixture resulting from amidation has a high solids content. Chlorination of the filtered "amide" mixture to form the cyclic 3-isothiazolone hydrochloride mixture (2) is conducted with the amide in a concentrated slurry in an organic solvent typically toluene, perchloroethylene, ethyl or tributyl acetate; reaction preferably involves concurrently feeding chlorine gas in the proper molar ratio (3–6, preferably 5, mols $Cl_2$/1 mol of amide) to the amide slurry in a reactor.

An aqueous slurry of magnesium oxide may be used to neutralize the filtered 3-isothiazolone hydrochloride reaction mixture to form the technical grade product. A metal nitrate stabilizer compound is subsequently added to the technical grade product prior to a final heat treatment step. Heat treatment is effective for removing or decomposing by-products. Other desirable steps in the preparation of the commercial 3-isothiazolone biocides will be illustrated in the subsequent examples or may be found in the prior art patents cited elsewhere herein, particularly U.S. Pat. No. 3,849,430.

We have now discovered that nitrosamines can be efficiently eliminated from 3-isothiazolone products by (I) removing the nitrosamine precursor from the amide intermediate reaction mixture or by (II) inhibiting formation of the nitrosamine precursor during the amidation reaction. Alternative processes have been developed for each of (I) and (II).

The stabilized 3-isothiazolone compositions which can be prepared according to the processes of the present invention are "substantially free" of nitrosamine precursors and nitrosamines, that is, they contain less than about 100 ppm of such materials, preferably less than 50 ppm. Even more preferred for sensitive applications or uses which require only minimal dilution, are compositions containing less than 20 ppm of precursors and nitrosamines. As will be demonstrated hereinafter, it is even possible to produce compositions with no detectable nitrosamine or precursor compounds.

Removal or partial removal of the precursor from the amide intermediate may be accomplished by separation techniques such as (a) ion exchange, (b) crystallization or recrystallization, or (c) solvent extraction (filtration and washing). These techniques are useful with the amide reaction mixture produced from a disulfide intermediate according to the prior art commercial process, or when utilizing an alternative process disclosed herein (below) for inhibiting formation of the nitrosamine precursor. When the 3-isothiazolone product must be essentially nitrosamine-free, as with cosmetic products, a combination of the two techniques is often to be preferred.

Recrystallization of N,N'-dimethyl-3,3'-dithiodipropionamide, from 2-propanol effectively removes the nitrosamine precursor N-methyl-3-(N'-methylamino) propionamide from the reaction mixture of the disulfide and methylamine (see Example 3 below). Filtration and methanol washing of the N,N'-dimethyl-3,3'-dithiodipropionamide wetcake (see Example 4, below) reduces the precursor N-methyl-3-(N'-methylamino) propionamide level from 5000 ppm to 400 ppm.

Removal of the nitrosamine precursor by selective ion exchange of the reaction mixture is also effective. Treatment of a methanolic solution of N,N'-dimethyl-3,3'-dithiodipropionamide with a sulfonic acid cation exchange resin (Amberlyst 15, a trademark of Rohm and Haas Company, Philadelphia, Pa.) provides good removal of N-methyl-3-(N'-methylamino)propionamide from the reaction mixture of the disulfide with monomethyl amine (see reaction 1, above). The resin may be regenerated with methanolic aqueous hydrogen chloride (Example 5, below). The ion exchange process may be represented as follows:

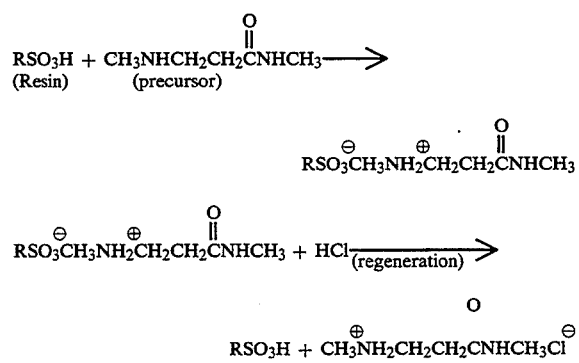

The final product 3-isothiazolone made from the ion exchange-treated intermediate has a much reduced nitrosamine content.

Formation of the nitrosamine precursors can be inhibited by use of a nucleophilic scavenger during the amidation reaction or by selection of different intermediates for the amidation reaction. Nucloephilic scavengers useful by the process of the invention are materials which are generally (a) more active than an amine in a Michael addition reaction but (b) which do not degrade the reactants or reaction product of the amidation (see Example 7 below). Most aliphatic and aromatic mercaptans are useful in the addition reaction to N-alkylacrylamide intermediates, which are the reactive compounds responsible for producing the principal nitrosamine precursors (see reactions 4 and 5 above). Other Michael addition reactants, such as sodium or potassium salts of alcohols are generally not as desirable because of their high reactivity with other starting materials. A higher concentration of the nucleophilic scavenger in the amidation reaction leads to proportionally greater reduction of the nitrosamine precursors:

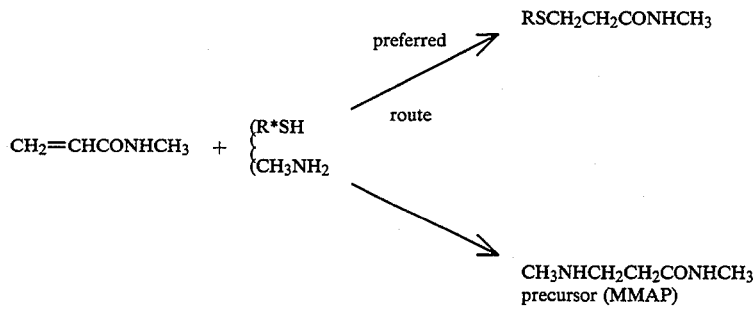

R* = e.g., methyl, ethyl, propyl, phenyl, etc. and also —CH$_2$CH$_2$COA—(alkyl) where A = O or NH.

The inherent avoidance of nitrosamine precursor when a mercaptan intermediate is selected in place of the normal disulfide intermediate in the amidation reaction is an important and unexpected finding of the present invention. A preferred mercaptan intermediate has the formula:

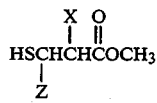

wherein X and Z have the meaning set forth above. The intermediate is essentially half of the conventional disulfide reactant (see reaction A above) used in the amidation reaction but, surprisingly, yields a product much lower in nitrosamine precursor, presumably by the same mechanism as postulated above for the nucleophilic scavengers. In the case of the isothiazolone biocide mixture illustrated above (in reactions 1-5) the mercaptan which may be used has the formula HSCH$_2$CH$_2$COOCH$_3$ and is known as "MMP" (methyl-3-mercaptopropionate). The remarkable reduction in nitrosamine precursor in the amide when using MMP in place of the usual disulfide is illustrated in the following table:

TABLE I

| Precursor* (CH$_3$NHCH$_2$CH$_2$CONHCH$_3$) Level in Intermediate Compared to MMP Process Intermediate | |
|---|---|
| Intermediate Batch | Precursor in Amide Reaction Mixture (ppm) |
| Amidated Disulfide Intermediate (Reaction 1 above) | |
| 1 | 5,600 |
| 2 | 4,800 |
| 3 | 6,400 |
| 4 | 4,500 |
| 5 | 5,000 |
| 6 | 10,100 |
| 7 | 11,400 |
| 8 | 5,700 |
| 9 | 9,400 |
| 10 | 6,700 |
| Amidated MMP Intermediate (HSCH$_2$CH$_2$CONHCH$_3$) | |
| 1, 2, 3 | 21, 24, 31 |
| 4 | 43 |
| 5 | 37 |
| 6 | 80 |
| 7 | 60 |
| 8 | 70 |
| 9 | <30 |
| 10 | <30 |

TABLE I-continued

| Precursor* (CH$_3$NHCH$_2$CH$_2$CONHCH$_3$) Level in Intermediate Compared to MMP Process Intermediate | |
|---|---|
| Intermediate Batch | Precursor in Amide Reaction Mixture (ppm) |
| 11 | 110 |

*Precursor = MMAP (see reaction 4, above).

Other advantages of using a mercaptan intermediate (e.g., MMP) may be found in the reaction product of the mercaptan and the amine. In the case of MMP, the amide is a liquid rather than a solid, as is the case with a disulfide intermediate (see Example 8). The difficulties usually encountered in handling, agitating, pumping and reacting a slurry are thus avoided. Further, use of the mercaptan intermediate reduces the amount of halogen (chlorine) needed for cyclization of the amide from the usual 3.0-6.0 mols/mol of intermediate to 2.8-3.4 mols, preferably 3.0 mols, per mol of intermediate.

The nitrosamine precursor by-product of the amidation reaction carries through to the final product, but the dilution of the AI in the product results in a lower concentration. Thus, the ultimate stabilized 3-isothiazolone composition will normally have a nitrosamine concentration of about 15% of the precursor concentration found in the amide. Table II illustrates the different concentrations of the major nitrosamine precursor (MMAP) in the amide compared to the nitrosamine (MMNP) in the corresponding stabilized (nitrate added/heat treated) product for a mixture containing (as the AI) 5-chloro-2-methyl-4-isothiazolin-3-one and 2-methyl-4-isothiazolin-3-one produced from an MMP starting material of the present invention.

TABLE II

| Precursor (MMAP) in Amide Intermediate v. Nitrosamine in Stabilized Product | | | |
|---|---|---|---|
| Amide Intermediate | | Stabilized 3-Isothiazolone | |
| Sample No. | MMAP (ppm) | MMNP* (ppm) | |
| 1 | 80 | <3 | |
| 2 | <30 | 2.0 | |
| 3 | 60 | <1.0 | |
| 4 | 70 | 7.3 | |
| 5 | <30 | ** | { 2.3 |
|  |  |  | 3.8 |
| 6 | <30 | | 1.9 |
| 7 | 110 | ** | { 10.6 |
|  |  |  | 3.4 |
|  |  |  | 8.3 |
| 8 | 21 | ** | { 1.0 |

TABLE II-continued

Precursor (MMAP) in Amide Intermediate v. Nitrosamine in Stabilized Product

| Amide Intermediate | | Stabilized 3-Isothiazolone |
|---|---|---|
| Sample No. | MMAP (ppm) | MMNP* (ppm) |
| 9 | 24 | 1.0 |
|  |  | 1.0 |
| 10 | 31 ** | 1.0 |
|  |  | 2.0 |
| 11 | 31 | 10.3 |
| 12 | 43 | 11.6 |
|  | ** | 7.9 |
|  |  | 3.6 |
| 13 | 37 | 6.0 |
|  | ** | 5.3 |
|  |  | 5.6 |

*MMNP = N-methyl-3-(N'-methyl-N'-nitroso)aminopropionamide (a nitrosamine) produced by nitrosating MMAP.
**Intermediate divided for multiple conversions to the final product.

The mechanism for nitrosamine reduction in the above MMP process appears to reside in the reduction of the nitrosamine precursor N-methyl-3-(N'-methyl) aminopropionamide (MMAP) in the amide. The amide disulfide source for the postulated N-methylacrylamide intermediate (reaction 4 above) is reduced to a minor reaction by-product. Also, the MMP starting material and N-methyl-3-mercaptopropionamide appear to compete successfully with monomethylamine to consume N-methylacrylamide and hence avoid formation of MMAP. These postulated alternative routes are as follows:

$CH_3NHCOCH_2CH_2 + HSCH_2CH_2CO_2CH_3 \rightarrow CH_3NHCOCH_2CH_2SCH_2CH_2CO_2CH_3$
$CH_3NHCOCH=CH_2 + HSCH_2CH_2CONHCH_3 \rightarrow (CH_3NHCOCH_2CH_2)_2S$ The net result is the reduction of MMAP levels from about 5,000–11,000 ppm for the disulfide process to about <100 ppm in the MMP process.

The following specific examples are offered to illustrate this invention but are not to be construed as limitations thereof.

EXAMPLE 1 (Comparative example—illustrates state of the art)

Step 1: Amidation Preparation of N,N'-dimethyl-3,3'-dithiodipropionamide Intermediate Charged to a vapor-tight reaction kettle was dimethyl-3,3'-dithiodipropionate (101 lb, 0.424 mol), laktane (131 lb.) and methanol (5.06 lb). The mixture was cooled to 15°–20° C. with agitation. Monomethylamine (32.8 lb, 1.06 mol) was added beneath the surface of the reaction mixture with agitation at 15°–20° C. and 5–10 psi over 2 hr. After completing the monomethylamine addition, the mixture was stirred at 15°–20° C. for 10 hr. A thick, pale-yellow slurry was obtained. At this time the unreacted monomethylamine and methanol by-product were distilled from the mixture at ~100 mmHg. After the distillation period, the yellow slurry was rotary vacuum dried and isolated without washing to provide crude, dry N,N'-dimethyl-3,3'-dithiodipropionamide (100 lb, 100% yield), containing 5,000 ppm N-methyl-3-(N'-methyl) aminopropionamide.

Step 2: Chlorination (oxidation cyclization)

Preparation of a mixture of 5-chloro-2-methyl-4-isothiazolin-3-one hydrochloride and 2-methyl-4-isothiazolin-3-one hydrochloride.

A slurry of the crude N,N'-dimethyl-3,3'-dithiodipropionamide reaction product of Step 1 was diluted with toluene and chlorinated to yield a slurry containing 5-chloro-2-methyl-4-isothiazolin-3-one hydrochloride and 2-methyl-4-isothiazolin-3-one hydrochloride and mother liquor.

Step 3: Filtration and Neutralization

The chlorinated slurry from Step 2 was neutralized with a magnesium oxide slurry to form the tech grade product.

Step 4: Formulation and Heat Treatment (Stabilization)

The Tech product made in Step 3 was formulated by adding magnesium nitrate hexahydrate, and transferring the mixture to a heat treatment kettle equipped with an agitator and a reflux condenser.

The product was heat treated for 4 hours and then allowed to cool to room temperature. The batch was filtered to remove small amounts of suspended solids. This gave a product with the following AI analysis:

| Components | Wt. % |
|---|---|
| 5-chloro-2-methyl-4-isothiazolin-3-one | 9.8 |
| 2-methyl-4-isothiazolin-3-one | 6.0 |
| Nitrosamine[a] | 750 ppm |

[a]N-methyl-3-(N'-methyl-N'-nitroso)aminopropionamide (MMNP).

EXAMPLE 2 (Comparative Example/Illustrates State of the Art and Removal by Filtration Step 1: Amidation Into a three-liter, 4-necked flask equipped with a mechanical stirrer, thermometer, gas dispersion tube and dry ice condenser with nitrogen inlet adapter, was placed dimethyl-3,3'dithiodipropionate (1,062.5 g, 4.46 mol), toluene (535.0 g) and methanol (55.0 g). The apparatus was purged with nitrogen and the mixture was cooled to 10° C. Monomethylamine (346.0 g, 11.14 mol) was added through the gas dispersion tube with stirring at 10°–20° C. over 2 hrs. After completing the monomethylamine addition, the mixture was stirred at 20° C. for 20 hrs. to complete the reaction. A thick, pale yellow slurry was obtained. At this time the unreacted monomethylamine and methanol by-product were distilled from the mixture at ~100 mmHg. The crude dry N,N'-dimethyl-3,3'-dithiodipropionamide intermediate (1,022.4 g, 97% yield) contained 11,000 ppm N-methyl-3-(N'-methyl)aminopropionamide.

A portion of the intermediate slurry was filtered, washed with toluene and dried. The dry intermediate contained 8,000 ppm of N-methyl-3-(N'-methyl)aminopropionamide.

Step 2: Chlorination

Preparation of a mixture of 5-chloro-2-methyl-4-isothiazolin-3-one hydrochloride and 2-methyl-4-isothiazolin-3-one hydrochloride.

A one-liter 3-necked round bottom flask was equipped with an overhead agitator, a feed line (outlet) and a condenser with a drying tube. Into this flask, 635.8 g of a slurry of N,N'-dimethyl-3,3'-dithiodipropionamide (with 8,000 ppm precursor) in toluene was placed and agitated.

A one-liter, 5-necked resin kettle (i.e., a chlorinator) was equipped with an agitator, a fritted glass gas dispersion tube for Cl$_2$ inlet, a thermometer, a condenser attached to an off-gas scrubber, and a feed line-inlet for intermediate slurry. The kettle was jacketed for ice-water circulation. The cooling system maintained the chlorination batch at 25°–30° C. The chlorinator was charged with a 108 g of toluene as a heel, and the agitator was started.

The slurry and $Cl_2$ were fed concurrently at a molar feed ratio of 5.2. Thus, 453 g of the slurry was charged over a 55-minute period at a rate of about 8.2 g/min., while 227 g of $Cl_2$ (gas) was fed at a rate of about 4.1 g min., using a calibrated flowmeter.

Step 3: Filtration and Neutralization

To the agitated chlorination slurry 20 g of water was added gradually. After 10 min. of agitation, the batch was allowed to settle, and the mother liquor was siphoned out using a dipstick. An additional 45 g of water was added, and additional mother liquor was removed.

To the hydrochloride wet cake was added 116 g of water. The mixture was neutralized to a pH 4.5 by gradually adding an aqueous MgO slurry. The neutralized material was transferred to a separatory funnel and a 469 g of an aqueous Tech grade was separated from the organic layer:

| Active Ingredient (Tech) | Wt % |
|---|---|
| 5-chloro-2-methyl-4-isothiazolin-3-one | 17.1 |
| 2-methyl-4-isothiazolin-3-one | 5.5 |

Step 4: Formulation and Heat Treatment (Stabilization)

The pH of the above Tech was adjusted to 2.9, and 46.5 g of magnesium nitrate hexahydrate and 7.24 g of water were added to 100 g of the AI with agitation to give a solution with the following composition:

| Component | Nominal Conc., Wt % |
|---|---|
| Total AI | 15.2 |
| $Mg(NO_3)_2$ | 17.4 |

The above formulated product was transferred to a 500 ml 3-necked round bottom flask equipped with an overhead agitator, a water-cooled condenser and a thermometer attached to a themo-watch and pneumatic pot lifter assembly supporting a heating mantle.

The formulated product was heat-treated at 95° C. for 4 hrs. The product, 153.7 g, was filtered to remove any trace amounts of solids, and analyzed.

| Components | Wt % |
|---|---|
| 5-chloro-2-methyl-4-isothiazolin-3-one | 10.1 |
| 2-methyl-4-isothiazolin-3-one | 5.0 |
| Nitrosamine* | 1200 ppm |

$$*CH_3N(NO)-CH_2CH_2CONHCH_3$$

EXAMPLE 3

Recrystallization of Crude N,N'-Dimethyl-3,3'-dithiodipropionamide (Removal of Nitrosamine Precursor)

Crude amide intermediate (disulfide produced/see Example 1, above), 140 g, was dissolved in 1750 g of boiling 2-propanol and the solution was filtered rapidly through a pre-heated Buchner funnel. The filtrate was kept overnight at 5°–10° C. in a refrigerator. The crystalline product was collected by filtration on a Buchner funnel, washed with a 560 g portion of cool methanol and dried on a rotary evaporator (35° C./20 mm of Hg/2 hours) to give 995 g of 99.1% pure intermediate m.p. 113°–115° C.

Next, 789.2 g of the crystallized amide intermediate was recrystallized from 2300 g of boiling 2-propanol to give 685.6 g of 99.9+% w/w amide intermediate, m.p. 113°–115° C.

Anal. calcd. for $C_8H_{16}N_2O_2S_2$: C,40.65; H,6.82; N,11.85; O,13.54; S,27.13. Found: C,40.29; H,6.83; N,11.61; O,13.57; S,27.38.

The N-methyl-3-(N'-methyl)aminopropionamide content was 0 ppm.

Nitrosamine-Free Product, Using Pure Amide Intermediate

Following the chlorination procedure described in Example 2, 152.6 g of recrystallized pure amide was chlorinated; the chlorination slurry was filtered and neutralized to give 537.9 g of Tech product, with a total AI of 21.5%.

A 350 g portion of this Tech product was formulated by dissolving 145.5 g magnesium nitrate hexahydrate in the product. The formulated product was heat-treated at 95° C. for 4 hours to give 495 g of 3-isothiazolone composition with the following ingredients:

| | |
|---|---|
| 5-chloro-2-methyl-4-isothiazolin-3-one | 10.3% |
| 2-methyl-4-isothiazolin-3-one | 5.0% |
| Nitrosamine, ppm | 0 |

Nitrosamine-free Products, from Pure Active Ingredient Isothiazolones

Alternatively, pure 2-methyl-4-isothiazolin-3-one, and pure 5-chloro-2-methyl-4-isothiazolin-3-one, can be obtained and formulated as above to give pure product. This material, with or without 95° C./4 hour heat treatment, was found to be nitrosamine-free.

EXAMPLE 4 (Precursor Removal by Solvent Extraction)

Into a three-liter, 4-necked flask equipped with a mechanical stirrer, thermometer, gas dispersion tube and dry ice condenser with nitrogen inlet adapter, was placed dimethyl-3,3'-dithiodipropionate (1062.5 g, 4.45 mol) toluene (295.0 g) and methanol (295.0 g). The apparatus was purged with nitrogen and the mixture was cooled to 10° C. Monomethylamine (304.7 g, 9.81 mol) was added through the gas dispersion tube with stirring at 10°–20° C. over 2 hrs. After completing the monomethylamine addition, the mixture was stirred at 20° C. for 20 hrs. to complete the reaction. A thick, pale yellow slurry was obtained. At this time, the unreacted monomethylamine, methanol and some toluene were distilled from the mixture at 100 mmHg over 8 hrs. The resulting slurry was rotary evaporated to give crude N,N'-dimethyl-3,3'-dithiodipropionamide (1058.9 g, 100% yield), containing 5,000 ppm N-methyl-3-(N'-methyl)aminopropionamide. A portion of the crude product (353.0 g was slurried in 784.5 g toluene) and vacuum filtered through a 2,000 ml course sintered glass funnel to give a toluene wet cake (419.1 g). The toluene wet cake was washed with cold (0° C.) methanol (352.4 g) to give the methanol wet cake (315.2 g). The methanol wet cake was dried in a vacuum desiccator at ambient temperature to give the washed, dried amide intermediate (251.1 g), 71% recovery), containing 400 ppm N-methyl-3-(N'-methyl)aminopropionamide.

Following the process steps 2, 3 and 4 described in Example 2, above, the dry N,N'-dimethyl-3,3'-dithiodipropionamide was converted to give 260 g of 3-isothiazolone product (pH 2.1) with the following composition:

| Components | Wt % |
|---|---|
| 5-chloro-2-methyl-4-isothiazolin-3-one | 12.0 |
| 2-methyl-4-isothiazolin-3-one | 2.7 |
| Nitrosamine | 25 ppm |

EXAMPLE 5 (Precursor Removal by Ion Exchange)

Unfiltered laktane (Example 1, above) process N,N'-dimethyl-3,3'-dithiodipropionamide was rotary evaporated in the laboratory to constant weight. The dried intermediate contained 10,000 ppm N-methyl-3-(N'-methyl)aminopropionamide.

Conditioned Amberlyst 15 sulfonic acid ion exchange resin (22.2 g of 45.1% w/w material in water, 10.0 g of dry resin) was washed into a 50 ml buret (1 cm diameter) with methanol (25 ml). The resin was rinsed on the column with methanol (500 ml) to give a resin bed volume of 28 ml.

The dry intermediate was dissolved in methanol to give a 19.9% w/w solution. This solution was passed through the resin column at ambient temperature and atmospheric pressure at a flow rate of 9.21 bed volumes per minute. The resin became saturated with N-methyl-3-(N'-methyl)aminopropionamide and break-through occurred after collecting 34 bed volumes. The total quantity of methanolic solution treated up to the break-through point was 737.2 g. Rotary evaporation of the eluent allowed recovery of the crude N,N'-dimethyl-3,3'-dithiodipropionamide (146.5 g, 99.9% recovery), containing 380 ppm N-methyl-3-(N'-methyl)aminopropionamide.

EXAMPLE 6 (Precursor Removal by Ion Exchange)

Into a one-liter, 4-necked flask equipped with a mechanical stirrer, thermometer, gas dispersion tube and dry ice condenser with nitrogen inlet adapter, was placed dimethyl-3,3'-dithiodipropionate (215.5 g, 0.904 mol) and methanol (118.0 g). The apparatus was purged with nitrogen and the mixture was cooled to $\sim 10°$ C. Monomethylamine (70.0 g, 2.25 mol) was added through the gas dispersion tube with stirring at 10°-20° C. over 2 hrs. After completing the addition, the mixture was stirred at 20° C. for 20 hrs. to complete the reaction. A thick, pale yellow slurry was obtained. At this time the unreacted monomethylamine and some methanol were distilled from the mixture at $\sim 100$ mmHg. After distillation, a portion of the slurry (17.2 g) was rotary evaporated to constant weight (8.0 g), giving the concentration of crude product in the slurry at 47% w/w. The 47% w/w slurry was 436.0 g, corresponding to 204.9 g of crude N,N'-dimethyl-3,3'-dithiodipropionamide (96% yield). The dry, crude product contained 9,000 ppm N-methyl-3-(N'-methyl)aminopropionamide.

Conditioned Amberlyst 15 sulfonic acid ion exchange resin (22.2 g of 45.1% w/w material in water, 10.0 g of dry resin) was washed into a 50 ml buret (1 cm diameter) with methanol (25 ml). The resin was rinsed on the column with methanol (500 ml) to give a resin bed volume of 28 ml.

The 47% w/w slurry in methanol was further diluted with methanol to provide a 20.0% w/w solution. This solution was passed through the resin column at ambient temperature and atmospheric pressure at a flow rate of 0.21 bed volumes per minute. The resin became saturated with N-methyl-3-(N'-methyl)aminopropionamide and break-through occurred after collecting 18 bed volumes of eluent. The total quantity of methanolic N,N'-dimethyl-3,3'-dithiodipropionamide solution treated up to the break-through point was 315.0 g (63.0 g of AI). Rotary evaporation of the eluent allowed recovery of the crude N,N'-dimethyl-3,3'-dithiodipropionamide (63.0 g, 100% recovery), containing 300 ppm N-methyl-3-(N'-methyl)aminopropionamide.

Following the procedure described in Example 2, 73.3 g of the above-mentioned intermediate was chlorinated, filtered and neutralized to give 217.5 g of Tech grade product.

A 60 g sample of this Tech grade product was formulated with 29.4 g of $Mg(NO_3)_2.6H_2O$ and 7.8 g of water. The formulated product was heat-treated at 95° C. for 4 hours, cooled and filtered to give about 97 g of 3-isothiazolone with the following composition:

| | Wt % |
|---|---|
| 5-chloro-2-methyl-4-isothiazolin-3-one | 11.7 |
| 2-methyl-4-isothiazolin-3-one | 3.5 |
| Nitrosamine, ppm | 33 |

EXAMPLE 7 (Inhibition of Precursor by Nucleophilic Scavenger)

Following the procedure of Example 2, Step 1, dimethyl-3,3'-dithiodipropionate (212.5 g, 0.892 mol), methyl-3-mercaptopropionate (18.4 g, 0.153 mol) and monomethylamine (69.0 g, 2.22 mol) were reacted. The intermediate slurry was rotary evaporated to give crude N,N'-dimethyl-3,3'-dithiodipropionamide (224.1 g, 98% crude yield), containing 1,000 ppm N-methyl-3-(N'-methyl)aminopropionamide.

This Example has been repeated using higher levels of a nucleophilic scavenger. The results of these experiments have established an essentially proportional reduction of nitrosamine precursor as higher concentrations of nucleophilic scavenger were used.

EXAMPLE 8 (Inhibition of Precursor by Mercaptan Reactant Route)

Step 1: Preparation of N-methyl-3-mercaptopropionamide (MMPA)

Into a one-liter, 4-necked flask equipped with a mechanical stirrer, thermometer, gas dispersion tube, and dry ice condenser with nitrogen inlet adapter, was placed methyl-3-mercaptopropionate (MMP, 504.7 g, 4.20 mol). The vessel was purged with nitrogen and the liquid was cooled to 10° C. Monomethylamine (163.0 g, 5.25 mol) was added through the gas dispersion tube with stirring at 10°-20° C. over 1 hr. After completing the addition, the mixture was stirred at 20° C. for 20 hrs. to complete the reaction. At this time the methanol by-product and unreacted monomethylamine were distilled from the mixture at $\sim 100$ mmHg. The resulting mixture was rotary evaporated to give crude N-methyl-3-mercaptopropionamide (500.8 g, 100% yield), containing <30 ppm N-methyl-3-(N'-methyl)aminopropionamide.

Step 2: Chlorination

The procedure described in Example 2 was modified in that N-methyl-3-mercaptopropionamide (MMPA) was used in place of N-N'-dimethyl-3,3'-dithiodipropionamide. Thus, a 31% solution of N-methyl-3-mercaptopropionamide in toluene and Cl₂ were fed concurrently at a molar feed ratio of about 3.2.

To 59.5 g of a toluene heel, 398.9 g of 31% MMPA solution was charged over a period of 55 minutes at a rate of 7.1 g per minute, while a 220 g of Cl₂ was fed concurrently at a feed rate of 4.0 g per minute.

Step 3: Filtration and Neutralization

Following the procedure described in Example 2, the chlorination slurry made above was worked-up and neutralized to give 355 g of Tech grade 3-isothiazolone with the following composition:

| 5-chloro-2-methyl-4-isothiazolin-3-one | 16.0% |
|---|---|
| 2-methyl-4-isothiazolin-3-one | 5.3% |

Step 4: Formulation and Heat Treatment (Stabilization)

Following the procedure described in Example 2, a 200 g portion of the Tech grade material made above was formulated by adding 87.7 g Mg(NO₃)₂.6H₂O and 2.1 g water. The formulated product was heat-treated, cooled and filtered to give 289 g of 3-isothiazolone product with the following composition:

| 5-chloro-2-methyl-4-isothiazolin-3-one | 12.2% |
|---|---|
| 2-methyl-4-isothiazolin-3-one | 3.9% |
| Nitrosamine | 3.9 ppm |

EXAMPLE 9 (Preparation of N-(n-octyl)-3-mercaptopropionamide by Mercaptan Reactant Route)

In a small multi-necked reaction vessel equipped with a magnetic stirrer and gas inlet was placed isopropanol (2 ml), methyl-3-mercaptopropionate (2.0 g, 16.64 mmol), and n-octylamine (2.19 g, 16.94 mmol). The reaction vessel was connected to a trap containing bleach to trap mercaptan vapors, and the reaction was stirred for 19.5 hours while the reaction temperature was held at 30°–35° C. Methylene dichloride was added and the crude product was transferred to a round bottom flask. Evaporation of the solvent under reduced pressure yielded crude N-(n-octyl)-3-mercaptopropionamide as an oily white solid in essentially quantitative yield.

The N-(n-octyl)-3-mercaptopropionamide of Example 9 may be converted to the corresponding 2-n-octyl-isothiazolin-3-one substantially free of nitrosamine and nitrosamine precursor.

EXAMPLE 10 (Preparation of N-propyl-3-mercaptopropionamide by Mercaptan Reaction Route)

In a small multi-necked reaction vessel equipped with a magnetic stirrer, reflux condenser, and gas inlet was placed isopropanol (2 ml), n-propylamine (1.00 g, 16.92 mmol), and methyl-3-mercaptopropionate (2.0 g, 16.64 mmol). The reaction vessel was connected to a trap containing bleach, and the reaction was stirred at 30°–35° C. for 19.5 hours. The crude reaction mixture was concentrated under reduced pressure to remove excess amine, solvent and methanol. A light yellow liquid was obtained, with essentially all N-propyl-3-mercaptopropionamide.

The N-propyl-3-mercaptopropionamide of Example 10 may be converted to the corresponding N-propyl-isothiazolin-3-one substantially free of nitrosamine and nitrosamine precursor.

EXAMPLE 11 (Combinations of Inhibition and Removal of Precursor)

Following the procedure of Examples 1–8 above, combined use of the illustrated techniques has been employed to produce isothiazolone products having drastically reduced or no nitrosamines or precursors whatsoever.

We claim:

1. A process for preparing a biologically active, metal nitrate salt-stabilized 3-isothiazolone composition substantially free of nitrosamine impurities and precursors thereof which comprises:

(a) preparing a biologically active 3-isothiazolone substantially free of a by-product compound containing an amine moiety capable of being nitrosated to a nitrosamine, or a nitrosamine compound derived therefrom, which 3-isothiazolone includes 5-chloro-2-methyl-3-isothiazolone and, optionally, one or more additional 3-isothiazolones of the formula:

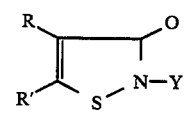

wherein R and R' are independently selected from hydrogen, halogen or an alkyl group of 1 to 4 carbon atoms; Y is an alkyl group of 1 to 8 carbon atoms, a cycloalkyl group of 5 or 6 carbon atoms, an aralkyl group of up to 8 carbon atoms, or an aryl or substituted aryl group of 6 carbon atoms by amidation of dimethyl dithiopropionate to form a dithioamide intermediate and undesirable by-product compound having amine moiety capable of being nitrosated;

(b) removing said undesirable by-product compound by a step selected from the group consisting of (i) ion exchange; (ii) recrystallization; and (iii) extraction with an organic solvent to form a dithioamide intermediate substantially free of undesirable by-product compound;

(c) chlorinating said dithioamide intermediate substantially free of undesirable by-product compound to form a 3-isothiazolone hydrochloride salt;

(d) neutralizing said 3-isothiazolone hydrochloride salt to form a biologically active 3-isothiazolone; and (e) adding to said 3-isothiazolone a ring-stabilizing metal nitrate salt in an amount sufficient to stabilize the ring of the 3-isothiazolone.

2. A method according to claim 1 wherein said biocidal composition comprises a mixture of 5-chloro-2-methyl-4-isothiazolin-3-one and 2-methyl-4-isothiazolin-3-one.

3. A method according to claim 1 wherein the 3-isothiazolone reaction product consists essentially of 60% to 90% by weight of 5-chloro-2-methyl-4-isothiazolin-3-one with the remainder 2-methyl-4-isothiazolin-3-one, and 0 to 20 parts of a nitrosamine of the formula

and its precursor CH$_3$NHCH$_2$CH$_2$CONHCH$_3$ per 150,000 parts of 3-isothiazolone.

4. A method according to claim 1 wherein the nitrate salt is either sodium nitrate, potassium nitrate, calcium nitrate, magnesium nitrate, copper nitrate, ferric nitrate, ferrous nitrate, nickel nitrate, zinc nitrate, barium nitrate, manganese nitrate, or cobalt nitrate, or mixtures thereof.

5. A method according to claim 1 wherein the nitrosamine impurities or precursors thereof comprise less than 50 parts per million by weight of the composition.

6. A method according to claim 1 containing less than 20 parts nitrosamine compound per 150,000 parts 3-isothiazolone compound.

7. A method according to claim 1 wherein the 3-isothiazolone reaction product contains no detectable nitrosamine or nitrosamine precursor compound.

* * * * *